(12) United States Patent
Heukensfeldt Jansen et al.

(10) Patent No.: US 12,708,331 B2
(45) Date of Patent: Aug. 18, 2026

(54) METHOD, SYSTEM AND/OR COMPUTER READABLE MEDIUM FOR CHARACTERIZING MOTION OF TISSUE BASED ON ACQUIRED PET DATA

(71) Applicant: GE Precision Healthcare LLC, Wauwatosa, WI (US)

(72) Inventors: Floribertus Philippus Martinus Heukensfeldt Jansen, Ballston Lake, NY (US); Matthew Gilbert Spangler-Bickell, Cambria, CA (US); Timothy Wayne Deller, Brookfield, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 495 days.

(21) Appl. No.: 18/213,403

(22) Filed: Jun. 23, 2023

(65) Prior Publication Data

US 2024/0423561 A1 Dec. 26, 2024

(51) Int. Cl.

*A61B 6/03* (2006.01)
*A61B 6/00* (2024.01)
*G06T 7/215* (2017.01)

(52) U.S. Cl.

CPC ............ *A61B 6/037* (2013.01); *A61B 6/5205* (2013.01); *A61B 6/5264* (2013.01); *G06T 7/215* (2017.01);

(Continued)

(58) Field of Classification Search

None

See application file for complete search history.

(56) References Cited

U.S. PATENT DOCUMENTS 11,179,128 B2 11/2021 Heukensfeldt Jansen et al.
2010/0266099 A1* 10/2010 Busch .................. A61N 5/1048 378/65

(Continued)

FOREIGN PATENT DOCUMENTS

| | | | | |
|---|---|---|---|---|
| CN | 104352245 A | * | 2/2015 | |
| CN | 106097384 A | * | 11/2016 | ............... G06T 5/73 |
| WO | WO-2017183958 A1 | * | 10/2017 | ............. G06T 7/251 |

OTHER PUBLICATIONS

Pepin et al, Management of respiratory motion in PET/computed tomography: the state of the art, Oct. 11, 2013 (Year: 2013).*

(Continued)

*Primary Examiner* — Fan Zhang
(74) *Attorney, Agent, or Firm* — Daugherty & Del Zoppo, Co. LPA

(57) ABSTRACT

A computer-implemented method includes obtaining positron emission tomography (PET) data of moving tissue of interest acquired over a plurality of motion cycles of the tissue of interest. The computer-implemented method further includes generating a set of short PET frames from the PET data based on a predetermined time duration, which is less than a period of the plurality motion cycles. The computer-implemented method further includes identifying the tissue of interest in each short PET frame in the set of short PET frames. The computer-implemented method further includes estimating a motion of the identified tissue of interest in each of the short PET frames. The computer-implemented method further includes characterizing the motion of the tissue of interest over the plurality of motion cycles based on the estimated motion of the identified tissue of interest in each of the short PET frames.

13 Claims, 12 Drawing Sheets

(52) U.S. Cl.
CPC ............... *G06T 2207/10104* (2013.01); *G06T 2211/412* (2013.01)

(56) References Cited

U.S. PATENT DOCUMENTS

| | | | | |
|---|---|---|---|---|
| 2013/0287278 | A1* | 10/2013 | Olivier .................. | G06T 11/003 382/131 |
| 2021/0181282 | A1 | 6/2021 | Deller et al. | |

OTHER PUBLICATIONS

EP application 24180060.6 filed Jun. 4, 2024—extended Search Report issued Nov. 12, 2024; 7 pages.

Klein G J et al: "Fine-scale motion detection using intrinsic list mode PET information", Mathematical Methods in Biomedical Image Analysis,, Dec. 9, 2001 (Dec. 9, 2001), pp. 71-78, XP010584861, DOI: 10.1109/MMBIA.2001.991701 ISBN: 978-0-7695-1336-2.

Lamare F et al: "PET respiratory motion correction: quo vadis?", Feb. 1, 2022, vol. 67, No. 3, Feb. 1, 2022 (Feb. 1, 2022), XP020415045, DOI: 10.1088/1361-6560/AC43FC [retrieved on Feb. 1, 2022].

* cited by examiner

METHOD, SYSTEM AND/OR COMPUTER READABLE MEDIUM FOR CHARACTERIZING MOTION OF TISSUE BASED ON ACQUIRED PET DATA

FIELD

The following generally relates to positron emission tomography (PET) and more particularly to characterizing motion of tissue based on acquired PET data.

BACKGROUND

Medical procedures target tissue of interest. For example, radiotherapy, which is a treatment procedure, applies radiation to a target tissue of interest, such as a tumor or lesion, to control or kill the target tissue of interest. During such a procedure, a treatment beam of radiation is directed at the target tissue of interest. However, certain autonomic nervous system (ANS) regulated physiological processes, such as breathing, the heart beating, etc., may cause the target tissue of interest to move. For example, breathing, which includes multiple cycles of inspiration and expiration, may cause the target tissue of interest to move in coordination with the cyclic motion of the lungs.

To track the treatment beam of radiation to a moving target tissue of interest during a procedure, the motion of the target tissue of interest has been estimated from a pre-procedure planning scan, and the estimated motion has been used during treatment planning to plan modulation of the treatment beam of radiation. In one instance, four dimensional (4D) cine computed tomography (CT) has been used to estimate the motion of the target tissue of interest. For this, for example, during a PET/CT planning scan, three dimensional (3D) volumetric CT image data is acquired over a respiratory cycle and images are reconstructed for the different phases of the respiratory cycle, collectively providing images of each phase of the respiratory cycle, and, hence, the location of the tissue of interest in each phase.

The motion of the target tissue of interest over the respiratory cycle has been estimated from the 4D cine CT image data and used for planning the radiotherapy procedure. However, 4D cine CT image data for a single respiratory cycle does not capture the variation in respiratory motion from respiratory cycle to respiratory cycle, which can be substantial. As a consequence, the target tissue of interest may move during the treatment procedure in a manner that was not anticipated from the 4D cine CT image data, and the treatment beam of radiation may not irradiate the target tissue of interest in accordance with the treatment plan. In addition, CT imaging utilizes ionizing radiation, which can damage and kill cells of healthy normal tissue, and, thus, it is not practical to acquire CT image data for multiple respiratory cycles.

In view of at least the foregoing, there is an unresolved need for an approach(s) for characterizing motion of tissue of interest.

SUMMARY

Aspects described herein address the above-referenced problems and others. This summary introduces concepts that are described in more detail in the detailed description. It should not be used to identify essential features of the claimed subject matter, nor to limit the scope of the claimed subject matter.

In one aspect, a computer-implemented method includes obtaining positron emission tomography (PET) data of moving tissue of interest acquired over a plurality of motion cycles of the tissue of interest. The computer-implemented method further includes generating a set of short PET frames from the PET data based on a predetermined time duration, which is less than a period of the plurality motion cycles. The computer-implemented method further includes identifying the tissue of interest in each short PET frame in the set of short PET frames. The computer-implemented method further includes estimating a motion of the identified tissue of interest in each of the short PET frames. The computer-implemented method further includes characterizing the motion of the tissue of interest over the plurality of motion cycles based on the estimated motion of the identified tissue of interest in each of the short PET frames.

A computer system includes a computer readable storage medium that includes instructions for characterizing motion of moving tissue of interest in PET data and a processor configured to execute the instructions. The instructions cause the processor to obtain PET data of the moving tissue of interest acquired over a plurality of motion cycles of the tissue of interest. The instructions further cause the processor to generate a set of short PET frames from the PET data based on a predetermined time duration, which is less than a period of the plurality motion cycles. The instructions further cause the processor to identify the tissue of interest in each short PET frames in the set of short PET frames. The instructions further cause the processor to estimate a motion of the identified tissue of interest in each of the short PET frames. The instructions further cause the processor to characterize the motion of the tissue of interest over the plurality of motion cycles based on the estimated motion of the identified tissue of interest in each of the short PET frames.

In another aspect, a computer readable medium is encoded with computer executable instructions. The computer executable instructions, when executed by a processor, cause the processor to obtain PET data of the moving tissue of interest acquired over a plurality of motion cycles of the tissue of interest. The computer executable instructions further cause the processor to generate a set of short PET frames from the PET data based on a predetermined time duration, which is less than a period of the plurality motion cycles. The computer executable instructions further cause the processor to identify the tissue of interest in each short PET frames in the set of short PET frames. The computer executable instructions further cause the processor to estimate a motion of the identified tissue of interest in each of the short PET frames. The computer executable instructions further cause the processor to characterize the motion of the tissue of interest over the plurality of motion cycles based on the estimated motion of the identified tissue of interest in each of the short PET frames.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Figure 1:
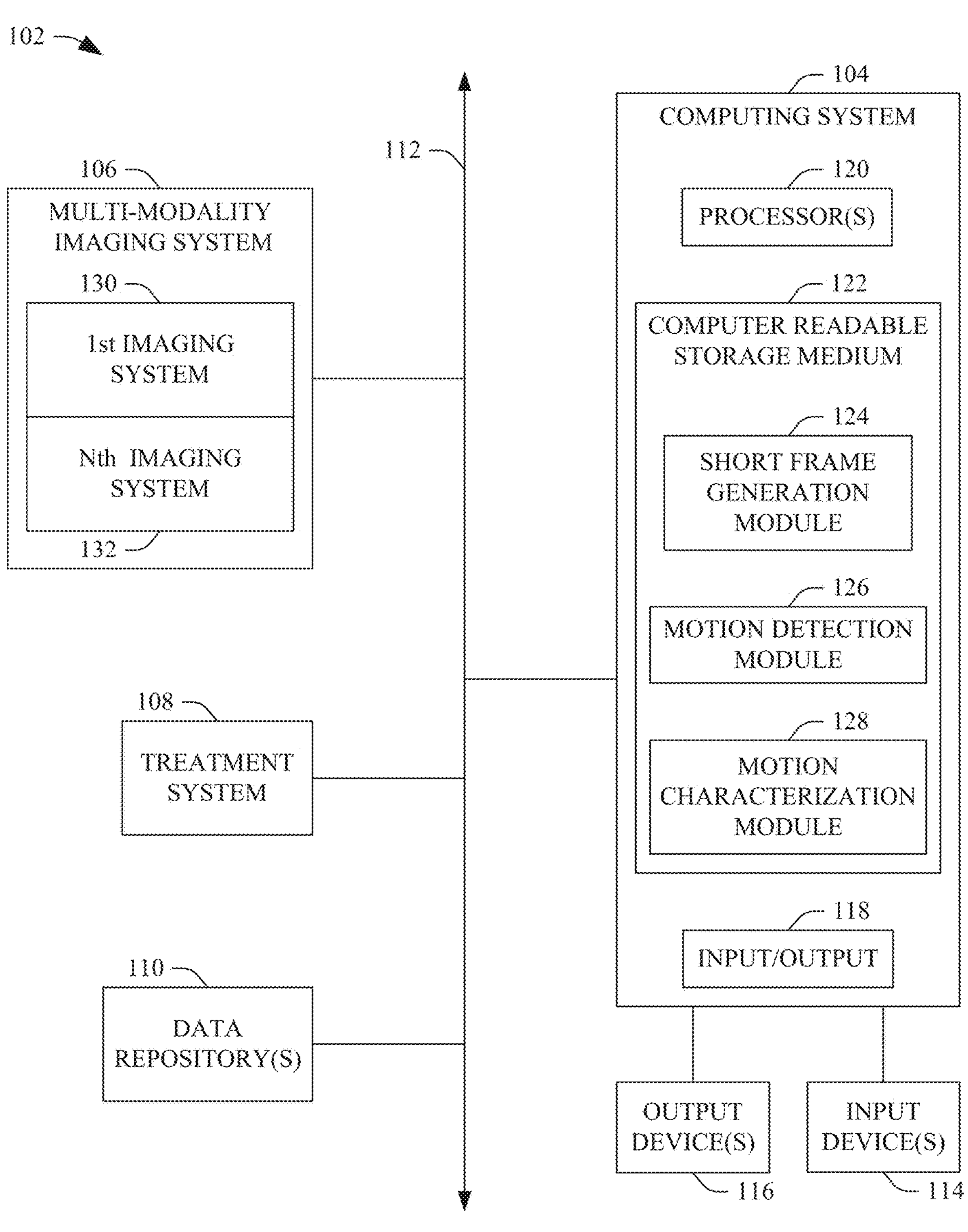
FIG. 1 schematically illustrates an example system, in accordance with an embodiment(s) herein.

Cyclic motion of certain tissue, e.g., the lungs, the heart, etc., can cause tissue of interest, such as a tumor(s), a lesion(s), lung tissue, heart tissue, etc., to move with each cycle of motion of the certain tissue. For procedures that rely on the location of the tissue of interest, such as radiotherapy, which apply a treatment beam of radiation to the tissue of interest, such motion has been estimated for a motion cycle from a pre-procedure scan, e.g., via 4D cine CT; however, the estimation does not fully describe the motion variation from cycle to cycle, which could lead to a less accurate and/or a less complete quantitation of tissue of interest motion and, thus, a less precise dose delivery during treatment. A computer-implemented method(s), a computing system(s) and/or a computer readable medium(s) described herein provide an approach(es) that overcomes at least such shortcomings.

In one instance, the approach(es) utilizes short PET frames, which are frames of PET data over a time duration that is less than a period of the motion cycles. As utilized herein, a short PET frame is any image-based representation of the acquired PET data, including, but not limited to images, point-cloud representations, back-projections, center-of-mass analyses of short-duration sinograms, etc. The time duration depends on the particular cycle, and not all cycles are the same duration. For example, the literature indicates that a normal respiratory rate of a person of the age of majority (i.e., eighteen and over) is twelve (12) to twenty (20) breaths per minute, which is three (3) to five (5) second breaths. For such a person, frames covering, e.g., a tenth of a second (0.1 s) to one second (1.0 s), such as ~0.5 s, would provide multiple short PET frames within each respiratory cycle over a plurality of respiratory cycles. The short PET frames cover multiple phases of the respiratory cycle, and, hence, multiple phases of the motion of the tissue of interest.

The tissue of interest is identified in each short PET frame, and the motion of the tissue of interest is tracked over the short PET frames, providing a position value of the tissue of interest in each short PET frame and, hence, each motion phase for all of the motion cycles. The approach(es), which is described in greater detail below, processes the position value to identify each cycle in the plurality of cycles, rebins the position value for the motion cycles into a plurality of bins (e.g., 20, 24, 30, etc.) each corresponding to a different phase of the motion cycles, and performs a statistical analysis across each bin to characterize the motion over the motion cycles. The motion characterization can then be utilized to plan a treatment, e.g., a radiotherapy treatment with a linear accelerator, for the tissue of interest. The treatment plan can then be utilized during the treatment to modulate the treatment beam based on the motion characterization. Examples of suitable modulation include adjusting an extent of the beam for a motion phase to cover an expected motion range, turning the beam off during certain motion phases, and/or otherwise modulating the beam.

In one instance, the approach(es) described herein facilitates pre-treatment planning with acquired PET data over multiple motion cycles, thereby allowing a more accurate and/or complete quantitation of tissue of interest motion, and, thus, a more precise dose delivery during treatment, without any additional radiation exposure/dose during acquisition, e.g., an additional 4D cine CT scan. The approach(es) described herein additionally mitigates using magnetic resonance (MR) imaging, ultrasound (US) imaging and/or X-ray imaging, which are based on different imaging properties relative to PET imaging, during treatment to determine motion of the tissue of interest in order to modulate the beam to track to the motion of the treatment tissue of interest. Embodiments of the present disclosure will now be described, by way of example, with reference to the Figures.

FIG. 1 schematically illustrates a non-limiting system 102. The non-limiting system 102 includes a computing system 104, a multi-modality imaging system 106, a treatment system 108, a data repository(ies) 110, and a computer network 112. In one instance, one or more of the computing system 104, the multi-modality imaging system 106, the treatment system 108 and the data repository(ies) 110 are in electrical communication with the computer network 112 and communicate over the computer network 112 with at least one other system also in electrical communication with the computer network 112, such as at least one of the computing system 104, the multi-modality imaging system 106, the treatment system 108 and the data repository(ies) 110. Such communication can be through a physically wired connection(s) and/or wireless technology(ies).

In one instance, the computing system 104 includes a computer, a workstation, a server, or the like. The computing system 104 includes an input device(s) 114 such as a keyboard, mouse, touchscreen, microphone, etc., an output device(s) 116 includes a human readable device such as a display monitor or the like, and input/output (I/O) 118 for transmitting and/or receiving signals and/or data. The computing system 104 further includes a processor(s) 120 such as a micro-processing unit (MPU), a central processing unit (CPU), a graphics processing unit (GPU), etc., and computer readable storage medium 122, which includes non-transitory medium (e.g., a storage cell or device) and excludes transitory medium (i.e., signals, carrier waves, and the like). The computer readable storage medium 122 is encoded with computer executable instructions and/or data.

The processor(s) 120 is configured to execute at least one of the computer executable instructions, employ and/or generate the data, etc. In one instance, the computer executable instructions include a short frame PET generation module 124, a motion detection module 126, and a motion characterization module 128. The short frame PET generation module 124 includes instructions for generating a short PET frame based on a pre-determined time duration, which is less than a period of the motion cycles, e.g., less than a period of a shortest motion cycle. The motion detection module 126 includes instructions for locating the tissue of interest in the short PET frames and determining tissue of interest position values based on the short PET frames. The motion characterization module 128 includes instructions for characterizing the detected motion over the motion phases over the captured motion cycles based on the tissue of interest position values.

The acquired PET data can be obtained by the computing system 104 over the computer network 112, e.g., via the multi-modality imaging system 106, the data repository(ies) 110, the radiation treatment system 108, and/or another apparatus. The characterized motion can be stored in the computer readable storage medium 122, the multi-modality imaging system 106, the data repository(ies) 110, the treatment system 108, and/or other apparatus. In another instance, at least one of the short frame PET generation module 124, the motion detection module 126 and/or the motion characterization module 128 is located in a different system such as the multi-modality imaging system 106, the treatment system 108, and/or other system, and the short PET frames and/or the position values are obtained by the system with the motion characterization module 128 and utilized to characterize the detected motion as such.

In one instance, the motion characterization, the short PET frames and/or the tissue of interest position values are stored, e.g., via a data structure, a file, etc., in the computer readable storage medium 122, the data repository(ies) 110, the treatment system 108, the multi-modality imaging system 106, and/or another apparatus. The motion characterization, the short PET frames and/or the tissue of interest position values can be transferred, e.g., in a header, metadata, a Digital Imaging and Communications in Medicine (DICOM) field, etc., or in a separate file, via the DICOM and/or other protocol.

The multi-modality imaging system 106 is configured with N imaging systems, including a $1^{st}$ imaging system 130, . . . , and an Nth imaging system 132, where N is an integer equal to or greater than one. In one instance, the multi-modality imaging system 106 is configured for at least two imaging modalities, including positron emission tomography (PET) imaging and computed tomography (CT) imaging or magnetic resonance (MR) imaging.

In one instance, one of the $1^{st}$ (or the Nth) imaging systems 130 (or 132) is configured for PET (or CT) imaging and the other of the $1^{st}$ or Nth imaging systems 130 or 132 is configured for CT (or PET) imaging. In general, the PET imaging system generates a functional data, and the CT imaging system generates a structural data. Examples of PET and CT imaging systems are described in further detail below.

In one instance, the multi-modality imaging system 106 generates the acquired PET data utilized by the short frame PET generation module 124 and the motion detection module 126 to produce the tissue of interest position values used by the motion characterization module 128 to characterize the detected motion. In such an instance the acquired PET data can be stored in the multi-modality imaging system 106, the computer readable storage medium 122, the data repository(ies) 110, the treatment system 108, and/or another apparatus.

The treatment system 108 includes, e.g., an external beam radiotherapy (EBRT) system. In one instance, the EBRT includes a radiation therapy system such as a linear accelerator (linac). In general, a radiation therapy system uses ionizing radiation to irradiate tissue of interest such as a tumor or a lesion to control or kill cells of tissue of interest. In another instance, the EBRT system includes a proton radiotherapy system such as a cyclotron, etc. In general, a proton radiotherapy system uses a beam of protons to irradiate tissue of interest such as a tumor or a lesion to control or kill cells of tissue of interest. In another instance, the EBRT system includes yet another therapy system. An example of the treatment system 108 is described in further detail below.

In one instance, the treatment system 108 generates and/or executes a treatment plan. The treatment plan is generated at least based on the motion characterization of the tissue of interest generated by the motion characterization module 128 of the computing system 104. In addition, the treatment plan includes modulation information for modulating the treatment beam to track the treatment beam to moving tissue of interest. The treatment plan can be stored in the treatment system 108, the data repository(ies) 110, the multi-modality imaging system 106, the computer readable storage medium 122, and/or another apparatus.

The system 102 further includes a data repository(ies) 110. In one instance, the data repository(ies) 110 includes a radiology information system (RIS), a hospital information system (HIS), an electronic medical record (EMR), a picture archiving and communication system (PACS), a server, a database, a cloud-based service, and/or other storage medium. In one instance, a data repository of the data repository(ies) 110 is remote to all of the computer readable storage medium 122, the multi-modality imaging system 106 and the treatment system 108. In another instance, a data repository of the data repository(ies) 110 is local to at least one of the computer readable storage medium 122, the multi-modality imaging system 106 and the treatment system 108.

Figure 2:
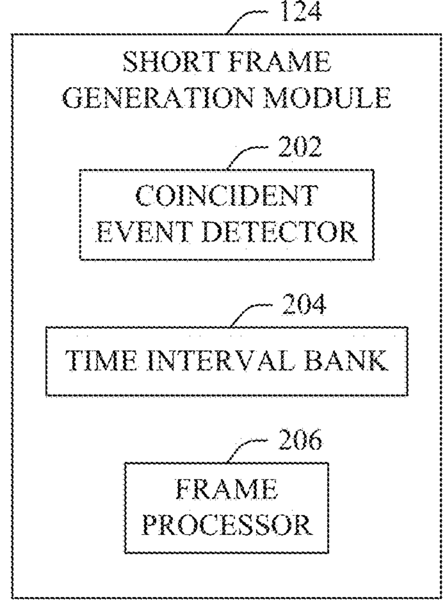
FIG. 2 schematically illustrates a non-limiting example of a short frame PET processing module, in accordance with an embodiment(s) herein.

FIG. 2 schematically illustrates a non-limiting example of the short frame PET generation module 124. The short frame PET generation module 124 receives, as input, acquired PET data of moving tissue of interest. The PET data includes at least event data from the tissue of interest that moved during the PET scan that acquired the PET data.

In one instance, the PET data is generated by the $1^{st}$ imaging system 130 or the Nth imaging system 132 of the multi-modality imaging system 106, whichever is configured for PET imaging. In another instance, the PET data is generated by one or more other imaging systems configured for PET imaging. The PET data can be obtained (e.g., received and/or retrieved) from the multi-modality imaging system 106, the one or more other imaging systems configured for PET imaging, the data repository(ies) 110, the treatment system 108, and/or other system.

The short frame PET generation module 124 includes a coincident event detector 202. The coincident event detector 202 is configured to identify coincident events in the PET data. For example, the coincident event detector 202 identify a pair of events as a coincident event where the events are detected along a line-of-response (LOR) within a predetermined time of each other to indicate coincidence. Pairs of detected events determined to be coincident events are recorded as coincident events. Events that cannot be paired are discarded.

The short frame PET generation module 124 includes a time interval bank 204. The time interval bank 204 includes at least one time duration that is used to define time windows over which to generate short PET frames. For example, where the motion cycle is the respiratory cycle, the at least one time duration may be ~0.5 seconds. In general, the time duration is based on the motion cycle of interest and is less than a period of the motion cycle of interest. Where short PET frames are generated for contiguous time windows, a first PET frame is generated with PET data acquired during the first 0.5 seconds of the scan, a next PET frame is generated with PET data acquired during the next 0.5 seconds of the scan, . . . , and a last PET frame is generated with PET data acquired during the last 0.5 seconds of the scan.

In another instance, one or more of the time windows may overlap. For example, a first PET frame may be generated with PET data acquired from 0.0 to 0.5 seconds of the scan, a next PET frame may be generated with PET data acquired from 0.4 to 0.9 seconds of the scan, . . . . In another instance, one or more of the time windows may include a time gap in between with PET data that is not utilized to generate a PET frame. For example, a first PET frame may be generated with PET data acquired from 0.0 to 0.5 seconds of the scan, a next PET frame may be generated with PET image data acquired from 0.6 to 1.0 seconds of the scan, . . . . Other overlap and/or time gaps are contemplated herein, including a varying overlap and/or time gap, e.g., based on the phase.

In one instance, the time interval is a default value. In one instance, the default value is a constant (e.g., ~0.5 seconds). In another instance, the time interval varies, e.g., where the cyclic motion varies. In another instance, the time interval bank 204 includes multiple time intervals. Such intervals may be based on the tissue of interest, the source of the cyclic motion, the imaging center, the radiologist assigned to read the PET data, etc. In another instance, an operator may change or specify the time interval, e.g., from a list of optional time intervals. In another instance, the short frame PET generation module 124 automatically selects a time interval from a list of optional time intervals based on, e.g., the tissue of interest, the source of the cyclic motion, etc.

The short frame PET generation module 124 further includes a frame processor 206. The frame processor 206 is configured to generate a short PET frame with the coincident pairs in the bin, for all of the bins in the data buffer and/or other memory. As such, each short PET frame will represent a phase within a motion cycle, and the set of short PET frames will represent the phases across multiple different motion cycles. The short frame PET generation module 124 can employ known iterative and/or other techniques to generate the short PET frames. In one instance, the frame processor 206 is configured to apply attenuation and/or scatter correction. In another instance, the frame processor 206 does not apply attenuation or scatter correction.

Figure 3:
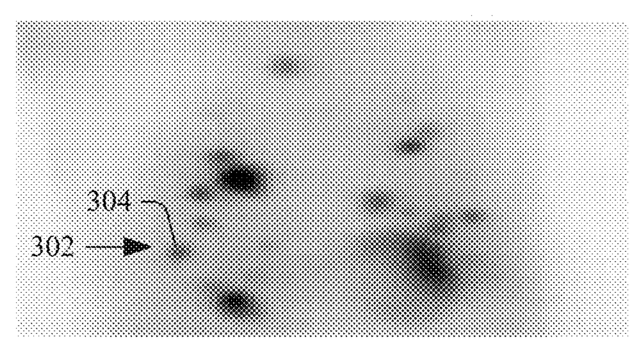
FIG. 3 includes a non-limiting example of a short PET frame, showing a location of tissue of interest in one phase, in accordance with an embodiment(s) herein.
Figure 4:
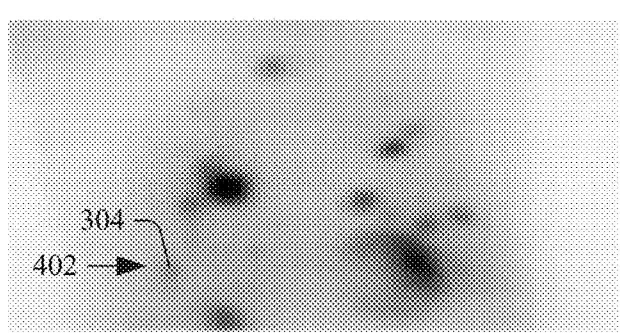
FIG. 4 includes a non-limiting example of a short PET frame, showing a location of the tissue of interest in another phase, in accordance with an embodiment(s) herein.
Figure 5:
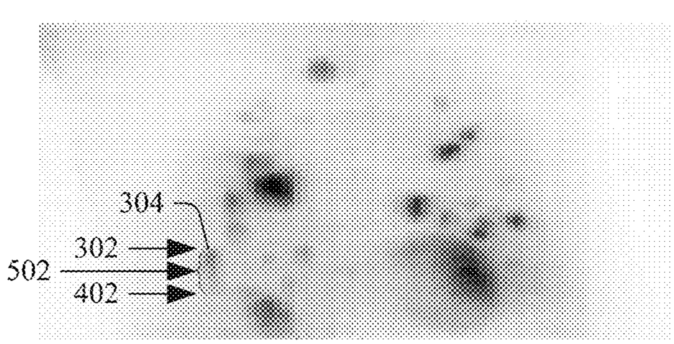
FIG. 5 includes a non-limiting example of a superposition of short PET frames for the tissue of interest across several of the short PET frames illustrating an extent of the motion over a plurality of motion cycles, in accordance with an embodiment(s) herein.

Each short PET frame in the set of short PET frames represents a phase of a corresponding motion cycle of the plurality of motion cycles, and a combination or superposition of the short PET frames represents the motion over the plurality of motion cycles. FIG. 3 provides a non-limiting example of one of the short PET frames, showing a location 302 of tissue of interest 304 in one phase, including motion of the tissue during the phase. FIG. 4 provides a non-limiting example of another of the short PET frames, showing a location 402 of the tissue of interest 304 in another phase, including motion of the tissue during the phase. FIG. 5 provides a non-limiting example of a superposition of such frames for the tissue of interest 304 across all of the frames, which shows an extent 502 of the motion. In FIG. 5, the locations 302 and 402 represent end points of the motion cycle.

Returning to FIG. 2, in another instance the frame processor 206 reconstructs short PET frames employing the algorithm(s) described in patent U.S. Pat. No. 11,179,128 B2, Ser. No. 16/732,250, filed on Dec. 31, 2019, and entitled "Methods and Systems for Motion Detection in Positron Emission Tomography," which is incorporated by reference in its entirety herein. In U.S. Pat. No. 11,179,128 B2, a series of live PET frames are generated during a defined time duration while acquiring the emission data. In a variation, the frame processor 206 employs the algorithm of U.S. Pat. No. 11,179,128 B2 to generate a set of short PET frames after the PET scan from the full acquired PET data and not during acquisition.

The set of short PET frames can be stored in the computing system 104, the multi-modality imaging system 106, the data the repository(ies) 110, the treatment system 108, and/or other apparatus.

Figure 6:
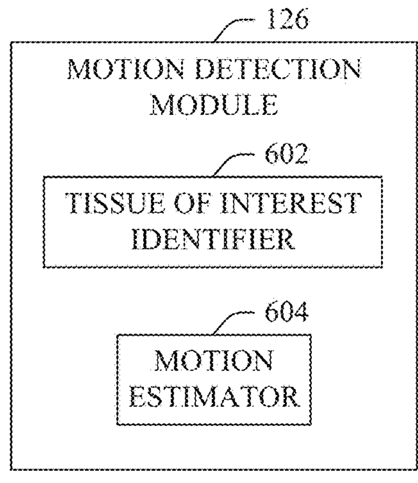
FIG. 6 schematically illustrates a non-limiting example of a motion detector module, in accordance with an embodiment(s) herein.

FIG. 6 schematically illustrates a non-limiting example of the motion detection module 126. The motion detection module 126 obtains, as input, the set of short PET frames generated by the frame processor 206 of the short frame PET generation module 124 and/or other processor. The set of short PET frames can be obtained (e.g., received and/or retrieved) from the multi-modality imaging system 106, the data the repository(s) 110, the treatment system 108, and/or other apparatus.

The motion detection module 126 includes a tissue of interest identifier 602. In one instance, the tissue of interest includes a tumor(s) or a lesion(s), and the tissue of interest identifier 602 identifies the tissue of interest in all or sub-set (less than all) of the set of short PET frames. The tissue of interest identifier 602 identifies the tissue of interest utilizing known and/or other segmentation approaches, including manual, semi-automatic and/or automatic segmentation approaches. Several suitable non-limiting examples of such approaches are discussed next.

A non-limiting approach includes K-means clustering. With this approach, K cluster centers are selected randomly or based on a heuristic approach, each pixel in the image is assigned to a cluster that minimizes a distance between the pixel and the cluster center, the cluster centers are then re-computed by averaging all of the pixels in the cluster, and the assigning and re-computing steps are repeated until stopping criteria (e.g., convergence where no pixels change clusters) is reached. K can be selected manually, randomly and/or by a heuristic, the distance is a squared or absolute difference between a pixel and a cluster center, and the difference can be based on pixel color, intensity, texture, and location, or a weighted combination thereof.

Another non-limiting approach includes a histogram-based approach, where a histogram is computed from the pixels in the image and the peaks and valleys in the histogram are used to locate clusters in the image via color or intensity. Another non-limiting approach includes edge detection such as search, zero-crossing and/or other edge detection techniques that find edges. Another non-limiting approach includes thresholding, which employs a threshold value(s) to turn a gray-scale image into a binary image. Another non-limiting approach includes artificial intelligence approach (e.g., pulse-coupled neural networks, U-Net, etc.). Another non-limiting approach includes a region-growing approach. Other approaches are also contemplated herein.

The motion detection module 126 further includes a motion estimator 604. The motion estimator 604 determines an absolute position, relative to a frame of reference, of the identified tissue of interest in two and/or three dimensions in all or a sub-set (less than all) of the short PET frames in which the tissue of interest is identified. The motion estimator 604 determines the position utilizing known and/or other approaches, including manual, semi-automatic and/or automatic approaches. Suitable non-limiting examples of such approaches are discussed next.

A non-limiting approach includes a center-of-mass analysis. In general, the center-of-mass is a weighted mean of the pixels and can be computed, e.g., by summing the pixels, each multiplied by its value, and dividing the result by a summation of the values. The center-of-mass provides the position of the center of each of the short PET frames. The center-of-mass of the short PET frames can then be tracked through the short PET frames to track the motion of the tissue of interest. Another non-limiting approach includes registering the frames to determine a displacement of the identified tissue of interest from frame to frame. Other approaches are contemplated herein.

Figure 7:
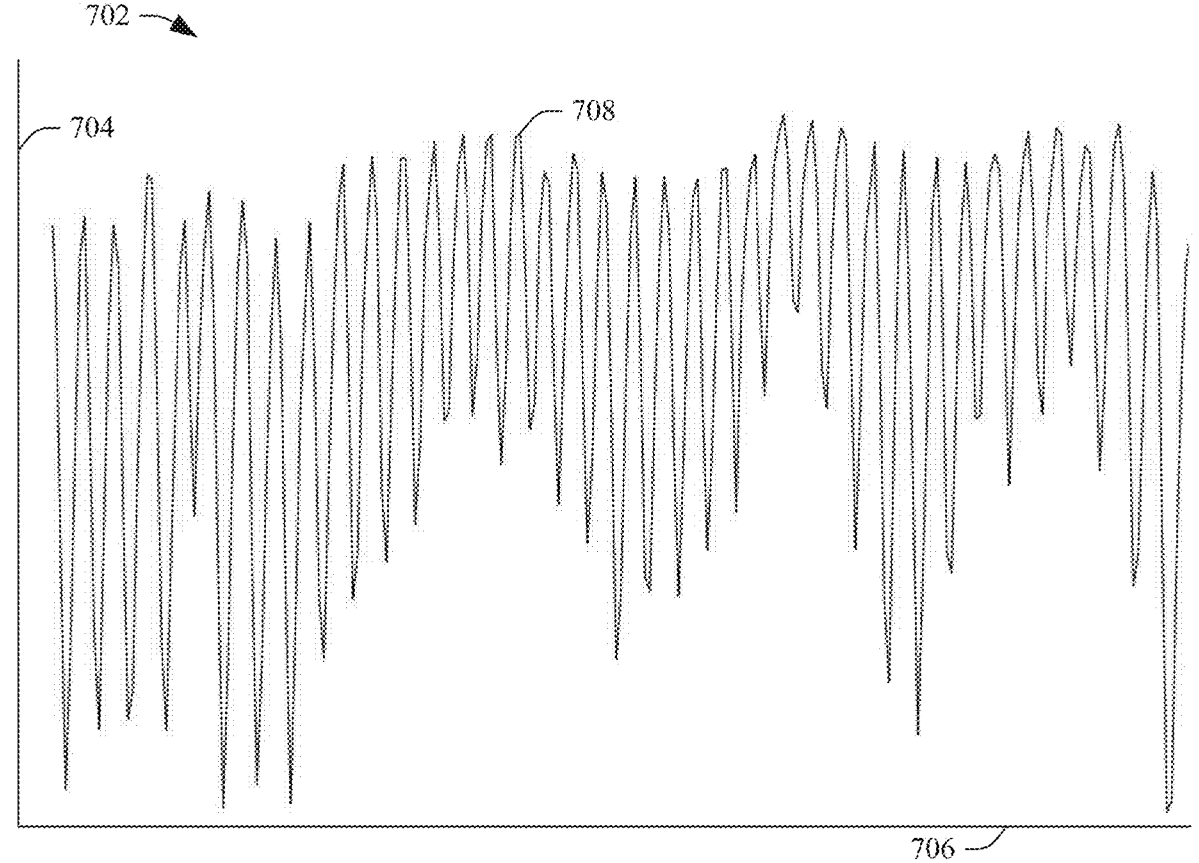
FIG. 7 graphically illustrates a non-limiting example of detected motion positions for a plurality of motion cycles, in accordance with an embodiment(s) herein.

The position of the tissue of interest in each short PET frame can be stored in a vector, a data structure, with the frame (e.g., in a header, metadata, a DICOM field, etc.), etc. Briefly turning to FIG. 7, a graphical representation 702 of an example of the set of positions is illustrated. The graphical representation 702 includes a first axis 704, which represents tissue of interest position, and a second axis 706, which represents the time. The illustrated graphical representation 702 includes a plot 708 of the tissue of interest position values over time. An example of the motion variation of each cycle is illustrated in the graphical representation 702, e.g., through the peaks and valleys.

Returning to FIG. 6, the set of positions of the tissue of interest (whether embedded with the corresponding short PET frames and/or separate therefrom) can be stored in the computing system 104, the data the repository(ies) 110, the multi-modality imaging system 106, the treatment system 108, and/or other apparatus.

Figure 8:
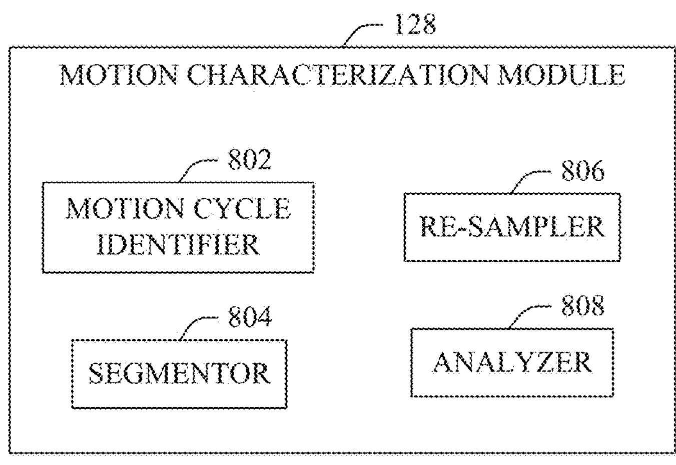
FIG. 8 schematically illustrates a non-limiting example of a motion characterization module of the non-limiting system, in accordance with an embodiment(s) herein.

FIG. 8 schematically illustrates a non-limiting example of the motion characterization module 128. The motion characterization module 128 obtains, as input, the set of position values of the tissue of interest determined by the motion detection module 126. In one instance, the motion characterization module 128 is configured to characterize the motion of the tissue of interest over all the motion cycles based on the set of positions of the tissue of interest. The set of positions can be obtained (received and/or retrieved) from the computing system 104, the data the repository(ies) 110, the multi-modality imaging system 106, the treatment system 108, and/or other apparatus.

The motion characterization module 128 includes a motion cycle identifier 802. The motion cycle identifier 802 identifies each cycle of motion of the tissue of interest based on the set of positions of the tissue of interest. In one instance, the motion cycle identifier 802 identifies each cycle based on local minimum and maximum values in the set of positions of the tissue of interest. In general, the minimum and maximum values identify inflection points, or points in the set of positions of the tissue of interest where motion of the tissue of interest changes direction.

Figure 9:
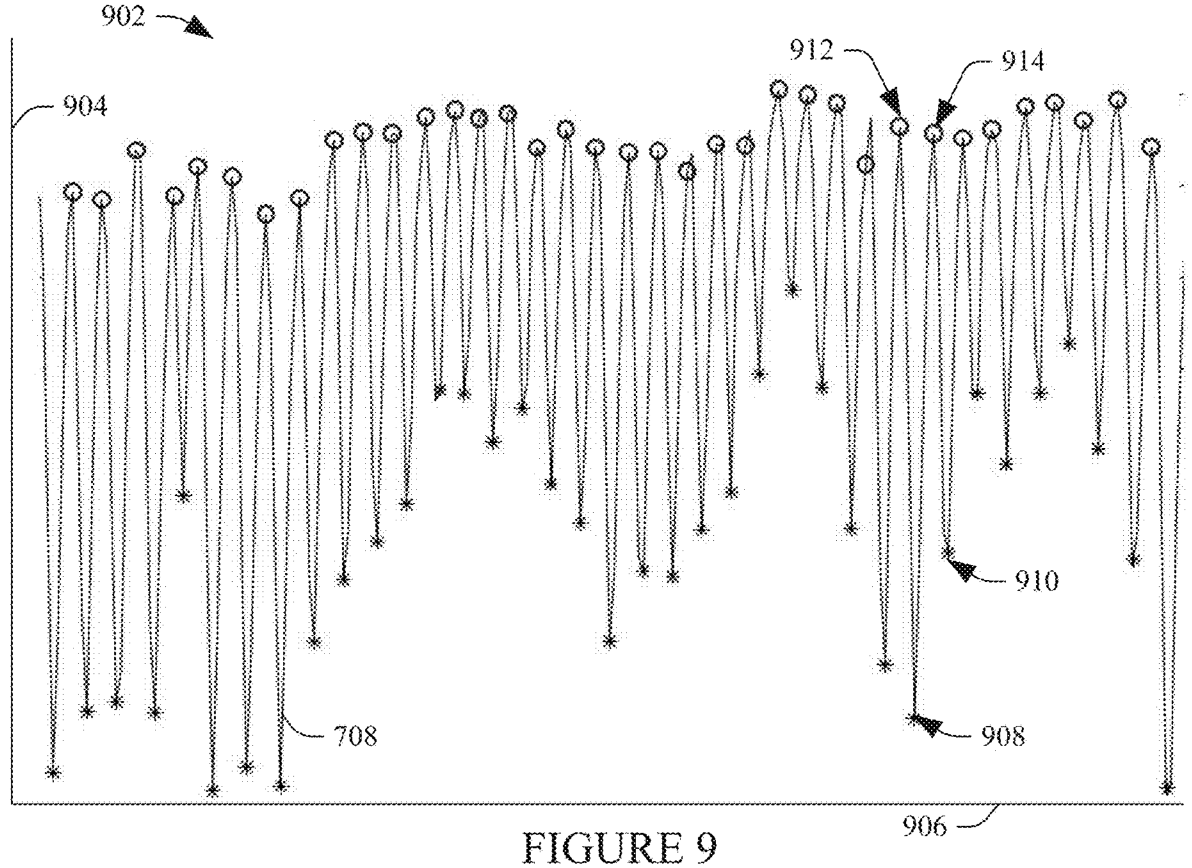
FIG. 9 graphically illustrates the non-limiting example of detected motion positions for the plurality of motion cycles with local minimums and maximums labeled, in accordance with an embodiment(s) herein.

Briefly turning to FIG. 9, a graphical representation 902 of an example set of tissue of interest position values, including local minimums and maximums, is illustrated. FIG. 9 is substantially similar to FIG. 7 with the addition of graphical symbols to identify local minimums and maximums. For example, FIG. 9 includes the plot 708 (FIG. 7) of the tissue of interest position values and additionally includes a graphical symbol identifying local minimums (e.g., at 908 and 910) and another graphical symbol "0" identifying local maximums (e.g., at 912 and 914).

Returning to FIG. 8, the motion cycle identifier 802 identifies a cycle from minimum to minimum or from maximum to maximum, e.g., identifies a start of each cycle based on the local minimums or maximum. Briefly turning to FIG. 10, a graphical representation 1002 of an example of a cycle from the local minimum 908 of FIG. 9 to the local minimum 910 of FIG. 9, passing through the local maximum 912 of FIG. 9, is illustrated. Briefly turning to FIG. 11, a graphical representation 1102 of an example of a cycle from the local maximum 912 of FIG. 9 to the local maximum 914 of FIG. 9, passing through the local minimum 908 of FIG. 9, is illustrated.

In the above, the motion can be derived from a full reconstruction, a point-cloud representation of the TOF data, a simple backprojection of the data, or center-of-mass analyses of short-duration sinograms, and/or otherwise.

Figures 10, 11, 12:
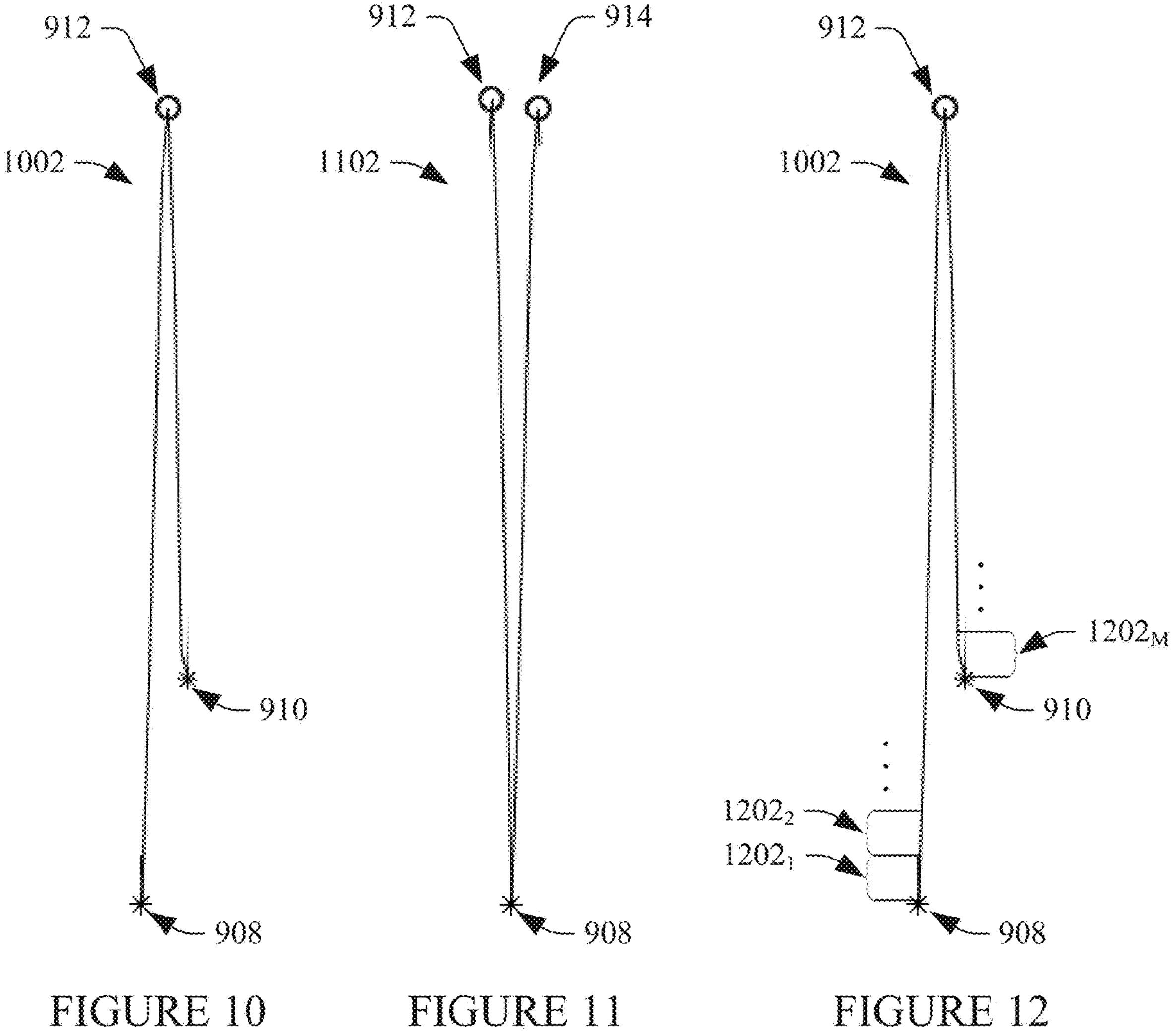
FIG. 10 graphically illustrates an identified cycle of the plurality of cycles from local minimum to local minimum, in accordance with an embodiment(s) herein.
FIG. 11 graphically illustrates an identified cycle of the plurality of cycles from local maximum to local maximum, in accordance with an embodiment(s) herein.
FIG. 12 graphically illustrates the identified cycle illustrated in FIG. 10 segmented into N segments, in accordance with an embodiment(s) herein.

Returning to FIG. 8, the motion characterization module 128 further includes a segmentor 804. The segmentor 804 is configured to segment each cycle into M segments, where M is an integer greater than one. Examples of M include 24, 15, 100, fewer, greater, etc. In one instance, M is a static value. In another instance, M is adjustable. The value of M can be a predetermined default. In another instance, M is user defined. Briefly turning to FIG. 12, the cycle 1002 in FIG. 10 is segmented into M segments, $\mathbf{1202}_1$, $\mathbf{1202}_2$ . . . , $\mathbf{1202}_M$, where a length of each segment corresponds to a displacement value, e.g., one millimeter (1 mm). etc. In one instance, the M segments are of equal size. In another instance, at least one of the M segments is a different size relative to another of the segments.

Returning to FIG. 8, the motion characterization module 128 further includes a re-sampler 806. The re-sampler 806 is configured to re-sample the position values in the set of positions of the tissue of interest from position values over time to bins of position values per segment. For example, the cycle 1002 in FIG. 12 is re-sampled into M bins such that the position values for the segment $\mathbf{1202}_1$ are in a $\text{bin}_1$, the position values for the segment $\mathbf{1202}_2$ are in a $\text{bin}_2$ . . . and the position values for the segment $\mathbf{1202}_M$ are in a $\text{bin}_M$. This is performed for a plurality of (e.g., all or multiple but not all) of the identified cycles, e.g., of the cycles shown in FIG. 9. As such, in one instance the bin will include all of the position values for the first segment of all of the cycles, etc.

Returning to FIG. 8, the motion characterization module 128 further includes an analyzer 808. The analyzer 808 is configured to determine statistics for each bin. Examples of statistics include, but are not limited to, a mean value, a standard deviation, etc. As such, in one instance the analyzer 808 computes a mean and standard deviation for each of the $\text{bin}_1$, the $\text{bin}_2$, . . . , and the $\text{bin}_M$. Briefly turning to FIG. 13, a graphical representation 1302 of an example of statistical data is illustrated. The graphical representation 1302 includes a first axis 1304, which represents tissue of interest displacement. The graphical representation 1302 further includes a second axis 1306, which represents the bins. The illustrated graphical representation 1302 includes a box plot with an inter-quartile range 1308 for each bin to indicate where motion is expected half of the time, a mean value 1310 for each inter-quartile range 1308, and whiskers 1312 extending from the inter-quartile ranges 1308 for each bin to indicate a range of motion outside of the inter-quartile ranges 1308.

Returning to FIG. 8, the statistical data can be stored in the computing system 104, the data the repository(ies) 110, the treatment system 108, the multi-modality imaging system 106, and/or other apparatus. The statistical data can be stored in a format similar to the box plot of FIG. 13 and/or other format.

Figures 14, 15, 16:
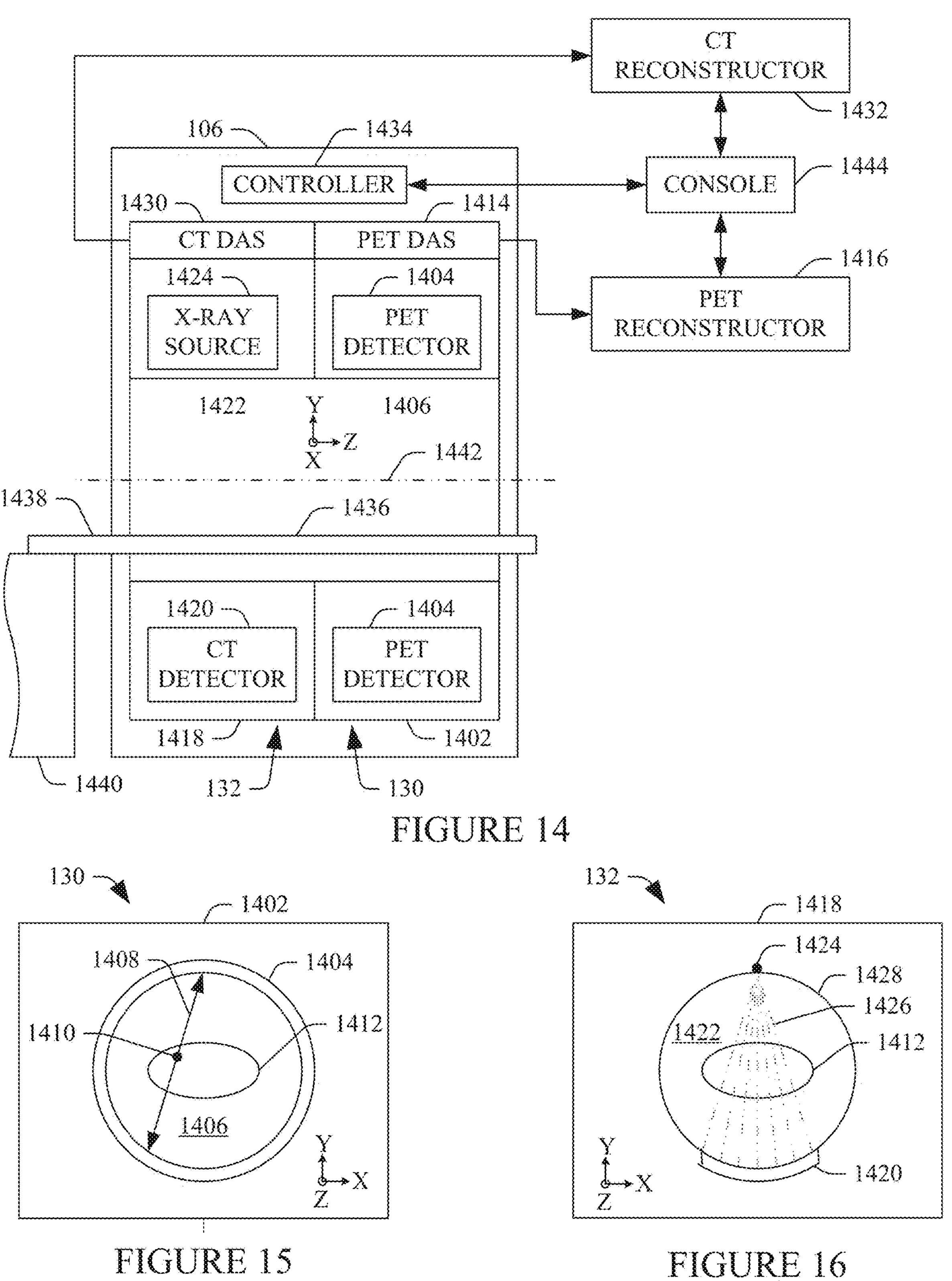
FIG. 14 schematically illustrates a non-limiting example of a cross-sectional side view of the multi-modality imaging system that includes a PET imaging system and a CT imaging system, in accordance with an embodiment(s) herein.
FIG. 15 schematically illustrates a non-limiting example of the PET imaging system, in accordance with an embodiment(s) herein.
FIG. 16 schematically illustrates a non-limiting example of the CT imaging system, in accordance with an embodiment(s) herein.

Turning to FIG. 14, a non-limiting example of a cross-sectional side view of a portion of the multi-modality imaging system 106 is schematically illustrated. The $1^{st}$ imaging system 130 is configured for PET imaging, and the Nth imaging system 132 is configured to CT imaging. FIG. 15 schematically illustrates a non-limiting example of a front view of the $1^{st}$ (PET) imaging system 130, and FIG. 16 schematically illustrates a non-limiting example of a front view of the Nth (CT) imaging system 132.

With reference to FIGS. 14 and 15, the $1^{st}$ computing system 104 includes a PET gantry 1402. The PET gantry 1402 includes a radiation sensitive detector array 1404 disposed about a PET examination region 1406 in a generally annular ring. The radiation sensitive detector array 1404 includes a plurality of detectors (detector crystals) in optical communication with a scintillator material (scintillation crystals), which is disposed between the plurality of detectors and the PET examination region 1406.

The scintillator material converts 511 keV gamma radiation 1408 produced in response to a positron annihilation event 1410 occurring in the examination region 1406 in a patient 1412 disposed therein into light photons, and the plurality of detectors convert the light photons into electrical signals. The plurality of detectors include one or more photosensors, such as avalanche photodiodes, photomultipliers, silicon photomultipliers, and/or another type of photosensor.

The $1^{st}$ imaging system 130 further includes a PET data acquisition system (DAS) 1414. The PET data acquisition system 1414 receives data from the radiation sensitive detector array 1404 and produces projection data, which includes a list of events detected by the plurality of radiation sensitive detectors 1404. The PET data acquisition system 1414 identifies coincident gamma pairs by identifying events detected in temporal coincidence (or near simultaneously) along a line of response (LOR), which is a straight line joining the two detectors detecting the events, and generates event by event, or list mode data indicative thereof.

Coincidence can be determined by a number of factors, including event time markers, which must be within a predetermined time period of each other to indicate coincidence, and the LOR. Events that cannot be paired can be discarded. Events that can be paired are located and recorded as a coincidence event pairs. The PET projection data provides information on the LOR for each event, such as a transverse position and a longitudinal position of the LOR and a transverse angle and an azimuthal angle.

Where the PET imaging system 130 is configured for time of flight (TOF), the PET projection data may also include TOF information, which allows a location of an event along a LOR to be estimated. For example, when a positron annihilation event occurs closer to a first detector crystal than a second detector crystal, one annihilation photon may reach the first detector crystal before (e.g., nanoseconds or picoseconds before) the other annihilation photon reaches the second detector crystal. The TOF difference may be used to constrain a location of the positron annihilation event along the LOR.

Additionally, or alternatively, the PET projection data is re-binned into one or more sinograms or projection bins. A PET reconstructor 1416 reconstructs the PET projection data using known iterative or other techniques to generate volumetric image data (i.e., PET image data) indicative of the distribution of the radionuclide in a scanned object. The PET image data can be co-registered with CT image data, and the CT image data can be utilized to generate an attenuation map for attenuation and/or other desired corrections to the PET image data.

In general, prior to a PET scan, a radionuclide (radiotracer) is administered to the patient. The radionuclide may include fluorine-18, carbon-11, nitrogen-13, oxygen-15, etc. The radionuclide may be incorporated into a molecule that is metabolized by the body or into a molecule that binds to a receptor target. As the radionuclide accumulates within organs, vessels, or the like, the radionuclide undergoes positron emission decay and emits a positron, which collides with an electron in the surrounding tissue.

When the positron collides with the electron, both the positron and the electron are annihilated and converted into a pair of photons, or gamma rays, each having an energy of 511 keV. The two photons are directed in substantially opposite directions and are each detected when they reach respective detectors positioned across from each other on the detector ring assembly. The two detectors detecting the coincident scintillation events are positioned substantially one hundred and eighty degrees from each other. When the photon impinges on the scintillation crystal a scintillation event (e.g., flash of light) is produced, and the detector crystal detects the scintillation event and produces a signal indicative thereof.

With reference to FIGS. 14 and 16, the Nth imaging system 132 includes a CT gantry 1418. The CT gantry 1418 includes a radiation sensitive detector array 1420 disposed about a CT examination region 1422 in an annular ring. The CT gantry 1418 further includes a radiation source 1424, such as an X-ray tube, that rotates about the CT examination region 1422. The radiation sensitive detector 1420 detects radiation 1426 emitted by the radiation source 1424 that has traversed the examination region 1422 and the subject 1412 therein.

The radiation source 1424 and the radiation sensitive detector array 1420 are disposed on a rotating frame 1428, opposite each other, across the CT examination region 1422. The rotating frame 1428 rotates the X-ray source 1424 in coordination with the array of X-ray radiation detectors 1420. The X-ray source 1424 emits X-ray radiation 1428 that traverses the examination region 1422 and the subject 1412 disposed therein, and the array of X-ray radiation detectors 1420 detect X-ray radiation impingent thereon. For each arc segment, the array of X-ray radiation detectors 1420 generate a view of projections.

A CT data acquisition system (DAS) 1430 processes the signals from the CT detectors 1420 to generate data indicative of the radiation attenuation along a plurality of lines or rays through the examination region 1422. A CT reconstructor 1432 reconstructs the data using reconstruction algorithms to generate volumetric image data (i.e., CT image data) indicative of the radiation attenuation of the object 1412. Suitable reconstruction algorithms include an analytic image reconstruction algorithm such as backprojection (FBP), etc., an iterative reconstruction algorithm such as advanced statistical iterative reconstruction (ASIR), a maximum likelihood expectation maximization (MLEM) algorithm, another algorithm and/or a combination thereof.

A subject support 1436 includes a tabletop 1438 moveably coupled to a frame/base 1440. In one instance, the tabletop 1438 is slidably coupled to the frame/base 1440 via a bearing or the like, and a drive system (not visible) including a controller, a motor, a lead screw, and a nut (or other drive system) translates the tabletop 1438 along the frame/base 1440 into and out of the examination region 1422 or 1406. The tabletop 1438 is configured to support an object or subject in the examination region 1422 or 1406 for loading, scanning, and/or unloading the subject or object.

In one embodiment, the multi-modality imaging system 106 includes a controller 1434 to control movement of the components such as rotation of the gantry 1428, the operation of the x-ray source 1424, operation of the detector arrays 1404 and 1420, operation of the subject support 1436, etc. For example, in one embodiment the controller 1434 includes an x-ray controller configured to provide power and timing signals to the x-ray source 1424. In another example, the controller 1434 includes a gantry motor controller configured to control a rotational speed and/or position of the gantry 1428 based on imaging requirements. In yet another example, the controller 1434 includes a subject support controller configured to control motion and/or height of the subject support 1436 for loading, scanning and/or unloading the patient 1412.

Figure 13:
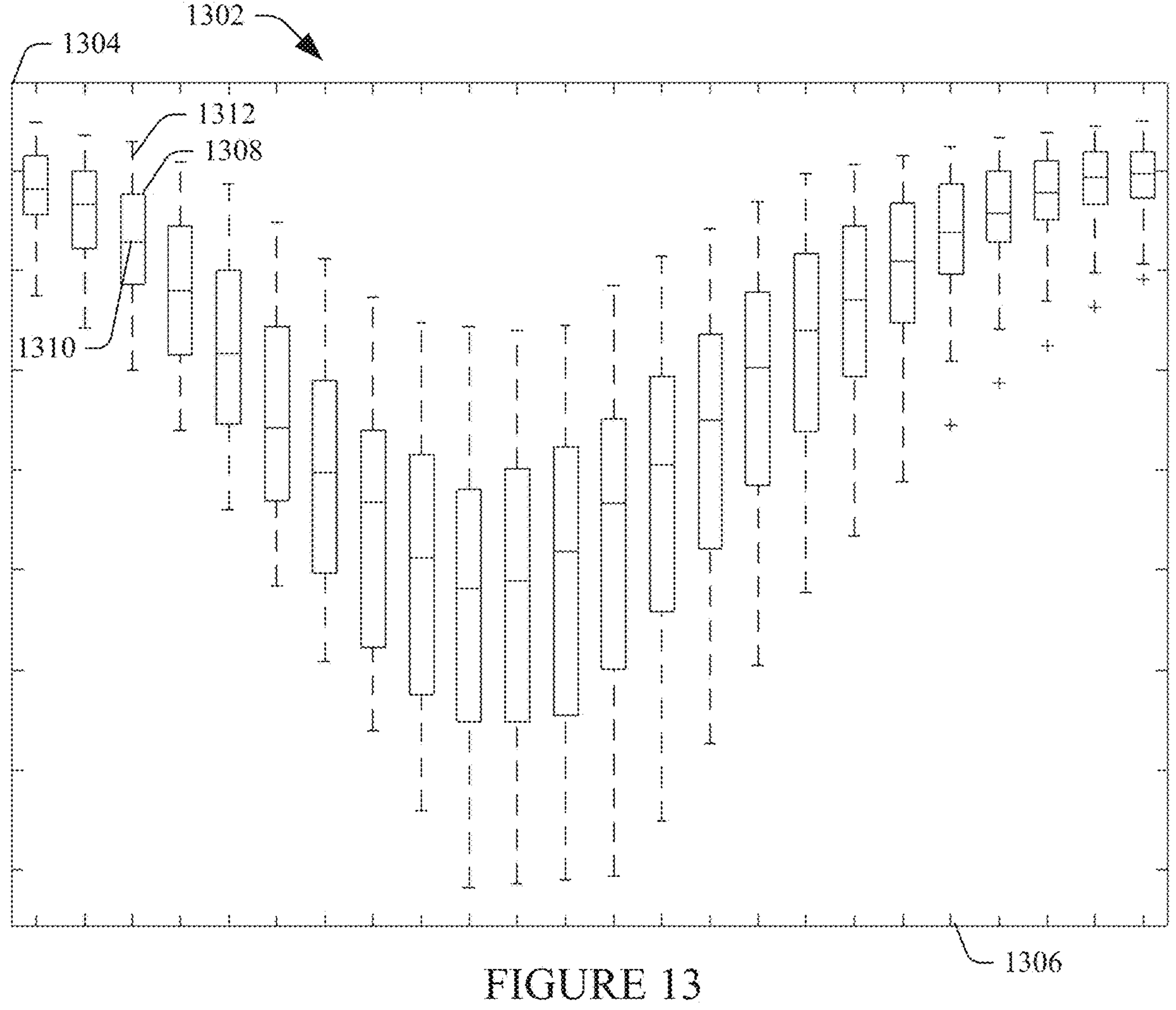
FIG. 13 graphically illustrates the motion position values statistically as a function of phase, in accordance with an embodiment(s) herein.

With reference to FIGS. 13, 14 and 15, in one instance the PET examination region 1406 and the CT examination region 1422 are disposed along a common longitudinal or z-axis 1442. The multi-modality imaging system 106 further includes an operator console 1444 configured to control the 1st and Nth imaging systems 130 and 132. The operator console 1444 can be substantially similar to the computing system 104 in that it may include a processor, computer readable storage medium, I/O interfaces, input and output devices, etc. In another instance, the 1st and Nth imaging systems 130 and 132 include their own operator consoles.

Figure 17:
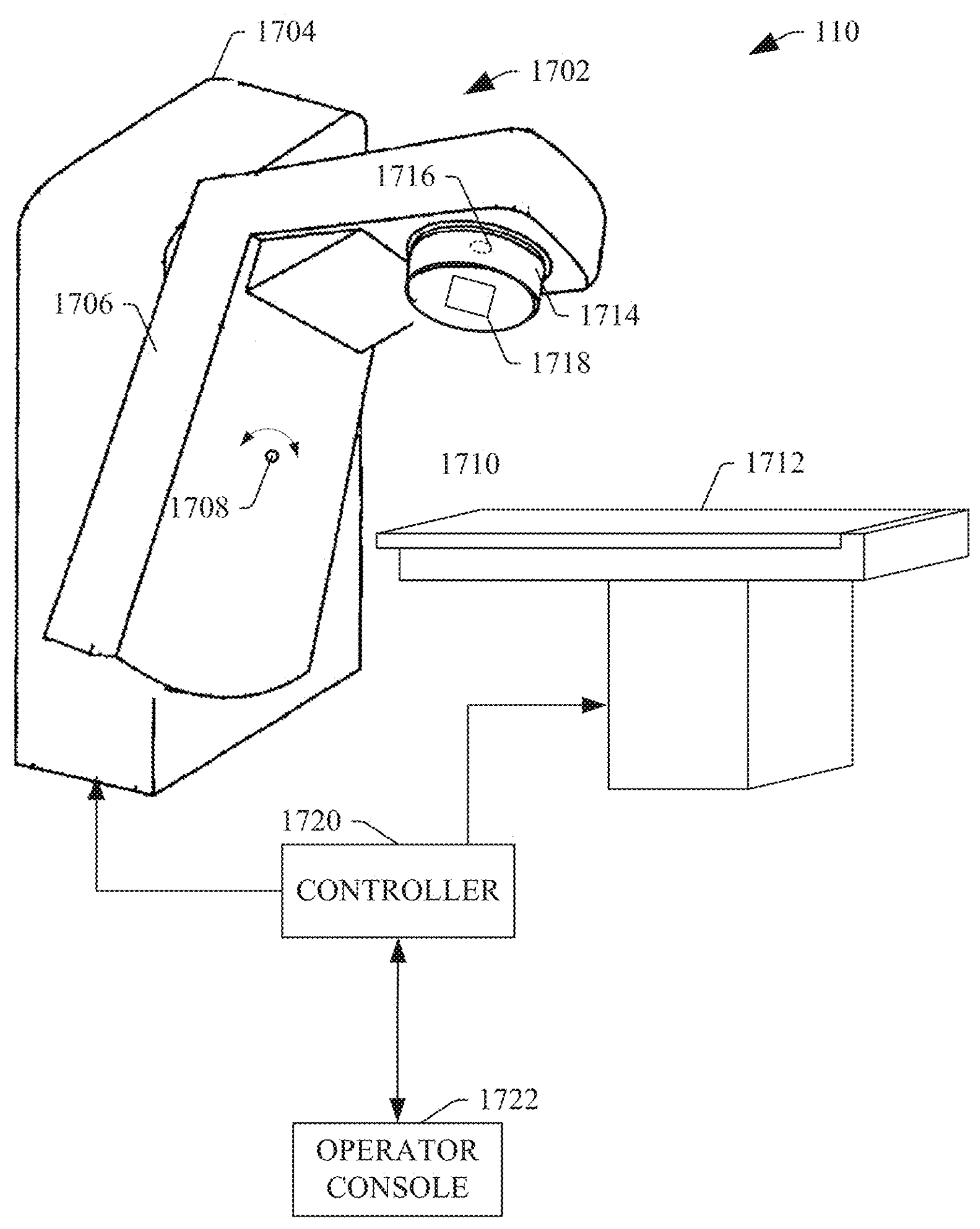
FIG. 17 schematically illustrates a non-limiting example of the treatment system, in accordance with an embodiment(s) herein.

FIG. 17 schematically illustrates a non-limiting example of the treatment system 110. In one instance, the treatment system 110 includes a linear accelerator 1702. The linear accelerator 1702 includes a stationary gantry 1704 and a rotating gantry 1706, which is rotatably attached to the stationary gantry 1704. The rotating gantry 1706 rotates (e.g., 180 degrees, etc.) with respect to a rotation axis 1708 about a treatment region 1710.

A subject support 1712 supports a portion of a subject in the treatment region 1710. The rotating gantry 1706 includes a treatment head 1714 with a therapy (e.g., a megavolt, MV) radiation source 1716 that delivers treatment radiation and a collimator 1718 (e.g., a multi-leaf collimator) that can shape the radiation fields that exit the treatment head 1714 into different shapes. The radiation source 1716 rotates in coordination with the rotating gantry 1706 about the treatment region 1710. The collimator 1718 includes a set of jaws that can move independently to shape a field.

A controller 1720 is configured to control rotation of the rotating gantry 1706 and deliver treatment radiation by the megavolt radiation source 1716 during a treatment such as an Intensity Modulated Proton Therapy (IMPT), Volumetric Modulated Arc Treatment (VMAT), and/or other radiation treatment. The controller 1720 is also configured to control the linear accelerator 1702 for one or more other modes such as step and shoot delivery at a set of beam positions, combined volumetric arc and step-and-shoot delivery and one or more co-planar or non-coplanar arc deliveries.

The linear accelerator 1702 includes an operator console 1722. The operator console 1722 can be substantially similar to the computing system 104 in that it may include a processor, computer readable storage medium, I/O interfaces, input and output devices, etc. The operator console 1722 may include a treatment planner module. In another instance, the treatment planner module is located on another computing system. The treatment planner generates radiation treatment plans.

In one instance, an operator employs the characterized motion generated by the motion characterization module 128 to facilitate generating a treatment plan via the treatment planner module. For example, in one instance characterized motion is employed to plan modulation of the treatment beam based on the expected motion of the tissue of interest. In one instance, the modulation includes varying an extent of the beam, e.g., via the collimator 1718. Additionally, or alternatively, the modulation includes turning off or blocking the beam (e.g., via the beam collimator 1718) so as not to irradiate the tissue of interest during certain phases, e.g., a phase with a large inter-quartile range based on the box plot of FIG. 13 and/or other information.

Figure 18:
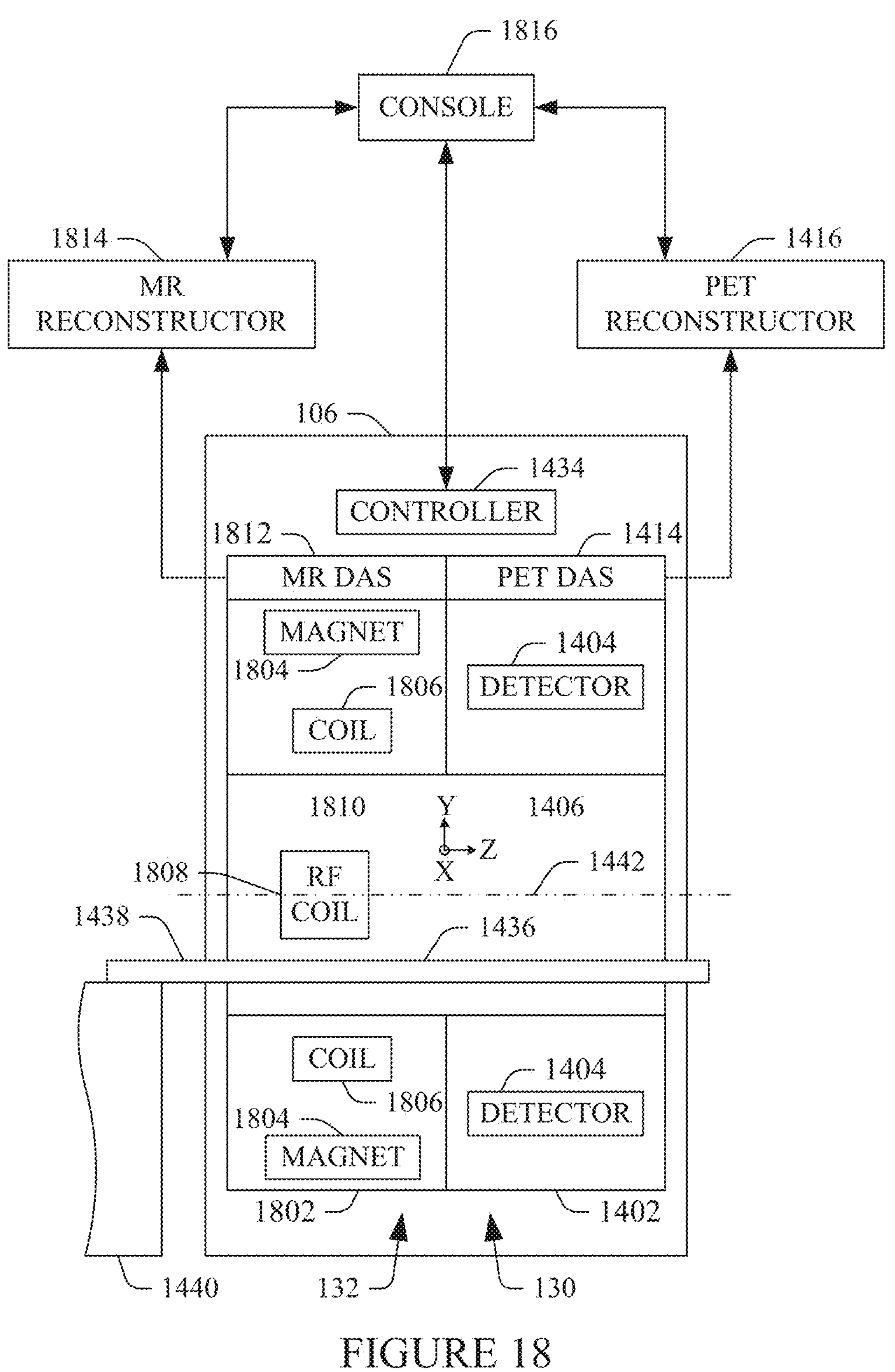
FIG. 18 schematically illustrates a non-limiting example of a cross-sectional side view of the multi-modality imaging system that includes the PET imaging system and an MR imaging system, in accordance with an embodiment(s) herein.

FIG. 18 schematically illustrates another non-limiting example of a cross-sectional side view of a portion of the multi-modality imaging system 106. The 1st imaging system 130 is configured for PET imaging as described in greater detail in connection with FIGS. 14 and 15. However, the Nth imaging system 132 is configured for MR imaging and will be described next.

The Nth imaging system 132 includes an MR gantry 1802. The MR gantry 1802 includes a main magnet 1804, a gradient (x, y, and z) coil(s) 1806, and a RF coil 1808. The main magnet 1804 (which can be a superconducting, resistive, permanent, or other type of magnet) produces a substantially homogeneous, temporally constant main magnetic field B0 in an MR examination region 1810. The gradient coil(s) 1806 generate time varying gradient magnetic fields along the x, y, and z-axes of the MR examination region 1810. The RF coil 1808 includes a transmit portion that produces radio frequency signals (at the Larmor frequency of nuclei of interest (e.g., hydrogen, etc.)) that excite the nuclei of interest in the examination region 1810 and a receive portion that detects MR signals emitted by the excited nuclei. In other embodiments, the transmit portion and the receive portion of the RF coil 1808 are located in separate RF coils 1808. A MR data acquisition system (DAS) 1812 processes the MR signals, and a MR reconstructor 1814 reconstructs the data and generates MR images.

The PET examination region 1406 and the MR examination region 1810 are disposed along the common longitudinal or z-axis 1442. The multi-modality imaging system 106 further includes an operator console 1816 configured to control the 1st and Nth imaging systems 130 and 132, including the subject support 1436 for both PET and MR scans. The operator console 1816 can be substantially similar to the computing system 104 in that it may include a processor, computer readable storage medium, I/O interfaces, input and output devices, etc. In another instance, the 1st and Nth imaging systems 130 and 132 include their own operator consoles.

In a variation, an external device such as a respiratory bellow, a spirometer, an optical tracker and/or the like can be used to detect the cyclic motion causing the tissue to move during the PET scan. The cyclic motion from the external device can then be correlated with and mapped to the motion characterization determined from the acquired PET data. Then, during the treatment and/or other procedure, the cyclic motion detected by the external device can be used to estimate the position of the tissue of interest based on mapping between the cyclic motion from the external device and the motion characterization determined from the PET data.

In another variation, the estimated motion provides a direct measurement of internal motion, which allows for amplitude-based gating without external hardware, which mitigates blurring due to the variation in amplitude with conventional gated imaging. With amplitude-based gating, which is a known technique, a particular gate is constructed from time intervals where the amplitude of motion reaches a particular point and a volume of data is generated based on the gate. In one instance, a set of motion amplitude ranges (i.e., gates) is determined based on the estimated motion. PET data from each motion cycle corresponding to a motion amplitude range of interest in the set of motion amplitude ranges is identified. The identified PET data is then combined to generate a frame of PET data. The results can be utilized to generate a movie that shows all the motion, while preserving full count statistics in every frame.

Figure 19:
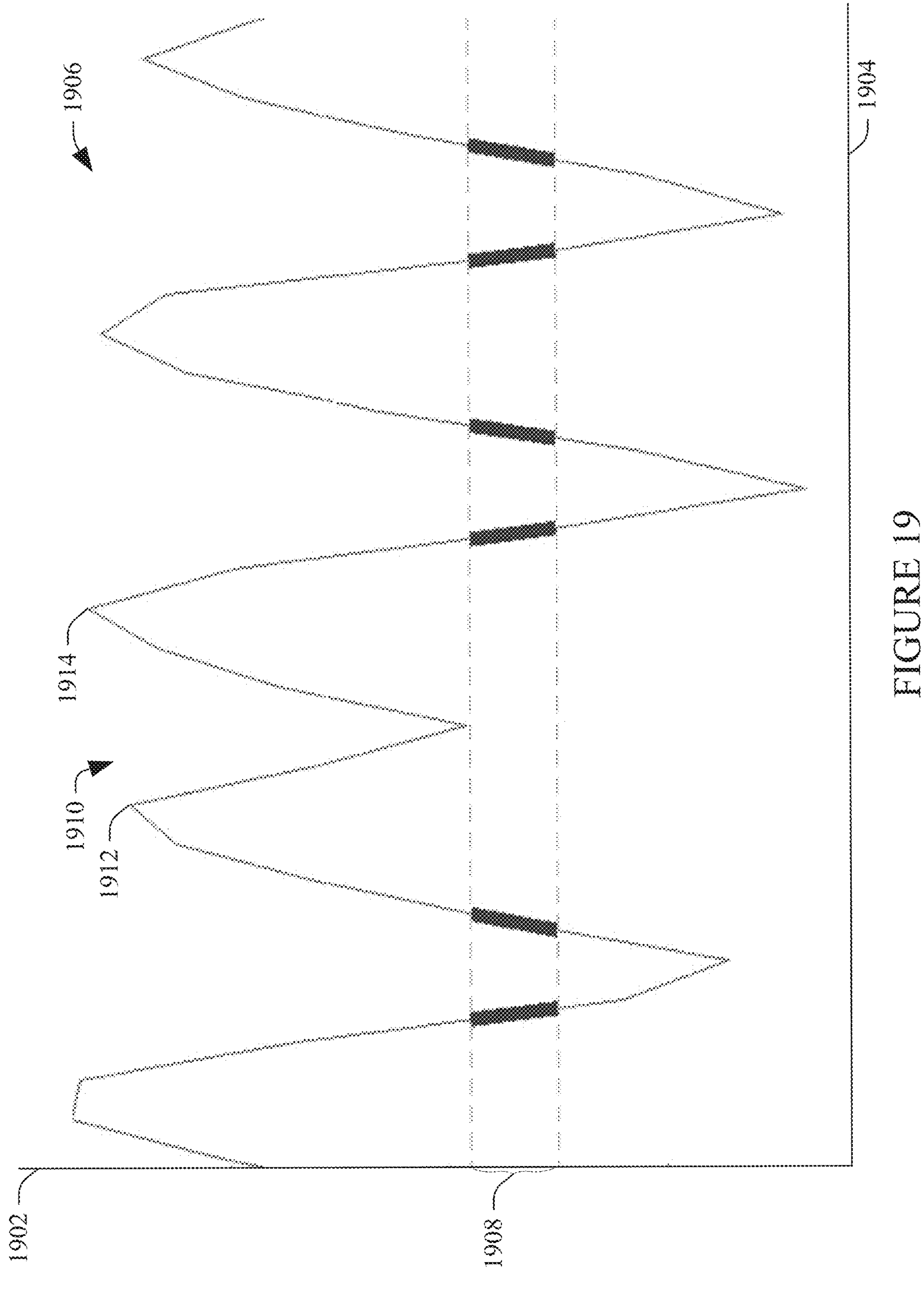
FIG. 19 graphically illustrates a non-limiting example of amplitude-based gating, in accordance with an embodiment(s) herein.

FIG. 19 graphically illustrates a non-limiting example of amplitude-based gating. A first axis 1902 represents amplitude, a second axis 1904 represents time, and a plot 1906 represents a plurality of the motion cycles. In the illustrated example, the estimated motion is utilized to determine a motion amplitude range of interest 1908. PET data from each cycle that corresponds to the motion amplitude range of interest 1908 is identified. As shown, one or more cycles (e.g., a cycle 1910 from 1912 to 1914) may not have PET data within the motion amplitude range of interest 1908. For such cycles, clearly no PET data is identified for the motion amplitude range of interest 1908. In general, depending on the amplitude of a given respiratory cycle, the relationship between trigger time and data aggregation varies.

Figure 20:
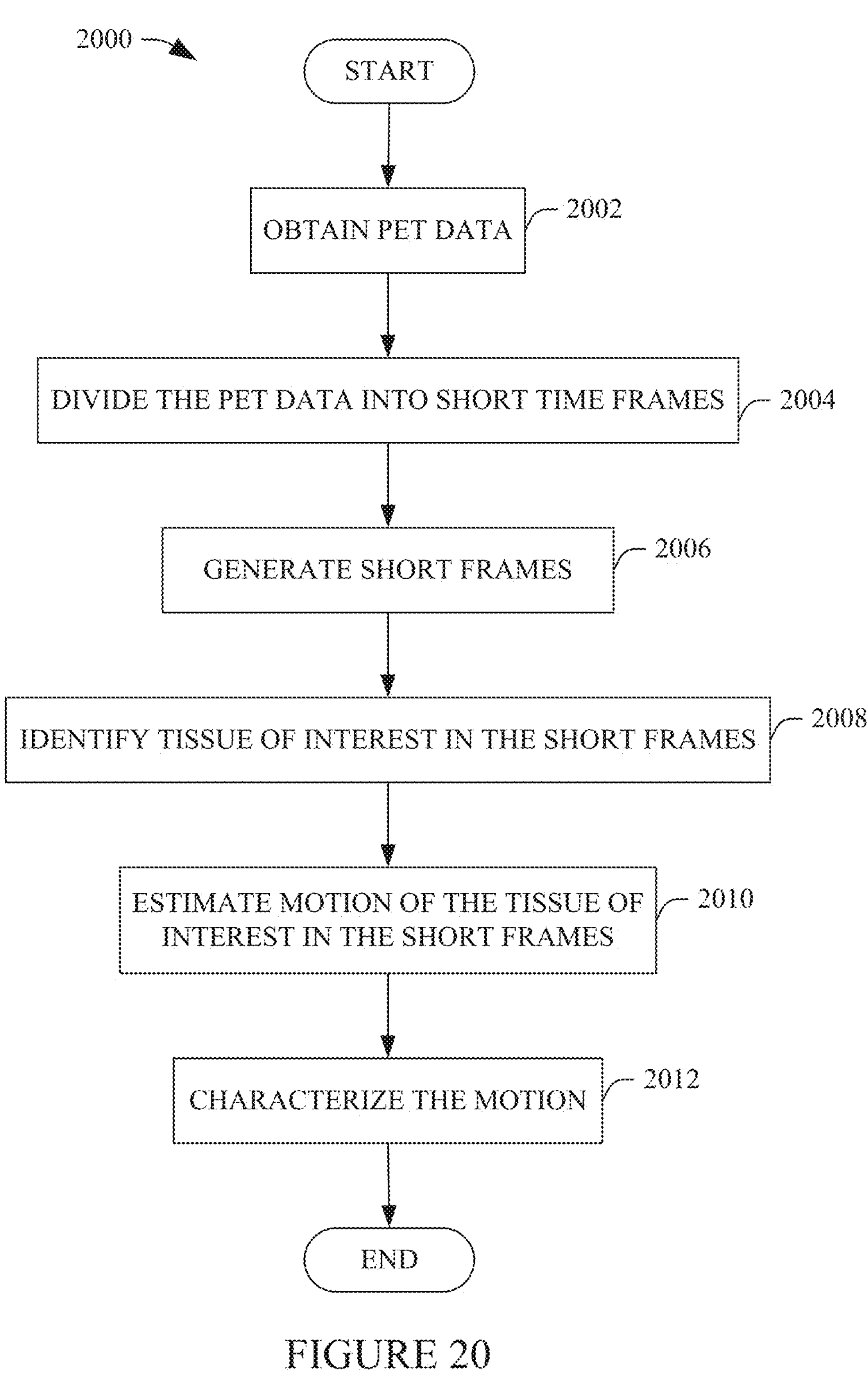
FIG. 20 illustrates a non-limiting example of a flow chart for a computer-implemented method, in accordance with an embodiment(s) herein.

FIG. 20 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 2002, PET data of moving tissue of interest is obtained, as described herein and/or otherwise. At 2004, the PET data is divided into a plurality of short time frames based on a predetermined time duration, as described herein and/or otherwise. At 2006, the divided PET data is processed to generate a set of short PET frames, as described herein and/or otherwise.

At 2008, the tissue of interest is identified in each of the short PET frames, as described herein and/or otherwise. At 2010, the motion of the tissue of interest is estimated with the set of short PET frames, as described herein and/or otherwise. At 2012, the motion of the tissue of interest is characterized based on the set of PET frames and the estimated motion, as described herein and/or otherwise. The characterized motion can be utilized, e.g., for planning a treatment and/or other procedure, as described herein and/or otherwise.

Figure 21:
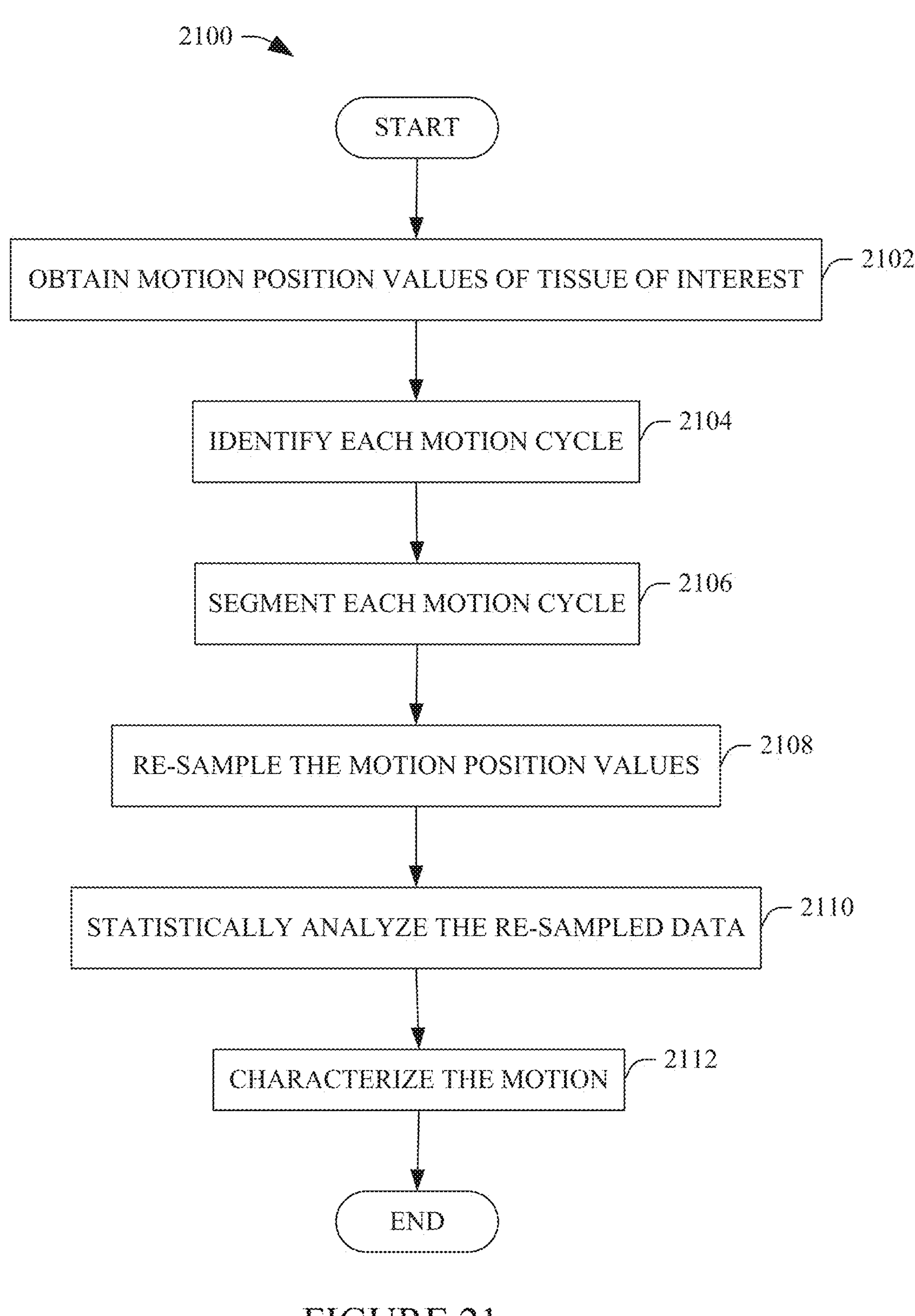
FIG. 21 illustrates another non-limiting example of a flow chart for a computer-implemented method, in accordance with an embodiment(s) herein.

FIG. 21 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included.

At 2102, motion position values of the tissue of interest (e.g., act 2010 of FIG. 20) determined from PET data of moving tissue of interest is obtained, as described herein and/or otherwise. At 2104, each cycle of motion of the tissue of interest of a plurality of motion cycles captured in the PET data is identified based on the obtained motion position values of the tissue of interest, as described herein and/or otherwise. At 2106, each cycle of motion of the tissue of interest is segmented into a plurality of segments, as described herein and/or otherwise.

At 2108, the position values of the tissue of interest are re-sampled from position values over time to bins of position values per segment, as described herein and/or otherwise. At 2110, the position values across each bin are statistically analyzed, as described herein and/or otherwise. At 2112, the motion is characterized based on a result of the statistical analysis, which characterizes the motion across the different phases of the motion cycle, as described herein and/or otherwise. The characterized motion can be utilized, e.g., for planning a treatment and/or other procedure, as described herein and/or otherwise.

The above method(s) can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising." "including." or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions that require them, but this should not be taken to mean that the features in the dependent claims are mutually exclusive.

What is claimed is:

1. A computer-implemented method, comprising:

obtaining positron emission tomography (PET) data of moving tissue of interest acquired over a plurality of motion cycles of the tissue of interest;

generating a set of short PET frames from the PET data based on a predetermined time duration, which is less than a period of the plurality of motion cycles;

identifying the tissue of interest in each short PET frame in the set of short PET frames;

identifying a position value of the identified tissue of interest in each short PET frame in the set of short PET frames;

identifying each of the plurality of motion cycles based on the position of the identified tissue of interest in each short PET frame in the set of short PET frames;

segmenting each identified cycle of the plurality of motion cycles into a predetermined number of segments, where a length of each segment corresponds to a predetermined displacement value;

re-sampling the position values of the plurality of motion cycles into bins corresponding to the segments;

determining statistics for each bin and therefore of the position values for each of the segments; and characterizing the motion of the tissue of interest over the plurality of motion cycles based on the statistics.

2. The computer-implemented method of claim 1, further comprising:

planning a procedure for the tissue of interest based on the characterization of the motion of the tissue of interest.

3. The computer-implemented method of claim 1, further comprising:

identifying local minimums in the position values, local maximums in the position values, or both local minimums and local maximums in the position values; and identifying each of the motion cycles based on the identified local minimums, local maximums, or local minimums and local maximums.

4. The computer-implemented method of claim 1, wherein the statistic incudes mean values and the standard deviations, and further comprising:

graphically presenting the mean values and the standard deviations.

5. The computer-implemented method of claim 1, further comprising:

determining a set of motion amplitude ranges based on the estimated motion;

identifying PET data from each motion cycle that corresponds to a motion amplitude range of interest in the set of motion amplitude ranges; and combining the identified PET data to generate a frame of PET data.

6. A computing system, comprising:

a computer readable medium memory that includes instructions for characterizing motion of moving tissue of interest in PET data; and a processor configured to execute the instructions, wherein the instructions cause the processor to:

obtain PET data of the moving tissue of interest acquired over a plurality of motion cycles of the tissue of interest;

generate a set of short PET frames from the PET data based on a predetermined time duration, which is less than a period of the plurality of motion cycles;

identify the tissue of interest in each short PET frames in the set of short PET frames;

identify a position value of the identified tissue of interest in each short PET frame in the set of short PET frames;

identify each of the plurality of motion cycles based on the position of the identified tissue of interest in each short PET frame in the set of short PET frames;

segment each identified cycle of the plurality of motion cycles into a predetermined number of segments, where a length of each segment corresponds to a predetermined displacement value;

re-sample the position values of the plurality of motion cycles into bins corresponding to the segments;

determine statistics for each bin and therefore of the position values for each of the segments; and characterize the motion of the tissue of interest over the plurality of motion cycles based on the statistics.

7. The computing system of claim 6, wherein the instructions cause the processor to:

identify local minimums in the position values, local maximums in the position values, or both local minimums and local maximums in the position values; and identify each of the motion cycles based on the identified local minimums, local maximums, or local minimums and local maximums.

8. The computing system of claim 6, wherein the instructions cause the processor to:

determine a mean value and a standard deviation for each bin; and characterize the motion of the tissue of interest based on mean values and standard deviations for the bins.

9. The computing system of claim 8, wherein the instructions cause the processor to:

graphically present the mean values and the standard deviations.

10. The computing system of claim 6, wherein the instructions cause the processor to:

perform amplitude-based gating without an external device based on the estimated motion of the tissue of interest over the plurality of motion cycles.

11. A non-statutory computer readable storage medium encoded with computer executable instructions, which when executed by a processor, causes the processor to:

obtain PET data of moving tissue of interest acquired over a plurality of motion cycles of the tissue of interest;

generate a set of short PET frames from the PET data based on a predetermined time duration, which is less than a period of the plurality of motion cycles;

identify the tissue of interest in each short PET frame in the set of short PET frames;

identify a position value of the identified tissue of interest in each short PET frame in the set of short PET frames;

identify each of the plurality of motion cycles based on the position of the identified tissue of interest in each short PET frame in the set of short PET frames;

segment each identified cycle of the plurality of motion cycles into a predetermined number of segments, where a length of each segment corresponds to a predetermined displacement value;

re-sample the position values of the plurality of motion cycles into bins corresponding to the segments;

determine statistics for each bin and therefore of the position values for each of the segments; and characterize the motion of the statistics.

12. The non-statutory computer readable storage medium of claim 11, where the instructions further cause the processor to:

identify local minimums in the position values, local maximums in the position values, or both local minimums and local maximums in the position values; and identify each of the motion cycles based on the identified local minimums, local maximums, or local minimums and local maximums.

13. The non-statutory computer readable storage medium of claim 11, where the instructions further cause the processor to:

identify PET data from each motion cycle that corresponds to a motion amplitude range of interest that was determined from the estimated motion; and combine the identified PET data to generate a frame of PET data.

* * * * *